(12) United States Patent
Faul et al.

(10) Patent No.: US 8,551,032 B2
(45) Date of Patent: *Oct. 8, 2013

(54) THERAPEUTIC METHOD FOR TREATMENT OF HYPERTENSION

(71) Applicants: John Faul, San Clemente, CA (US); Toshihiko Nishimura, San Clemente, CA (US); Peter Kao, San Clemente, CA (US); Ronald Pearl, San Clemente, CA (US)

(72) Inventors: John Faul, San Clemente, CA (US); Toshihiko Nishimura, San Clemente, CA (US); Peter Kao, San Clemente, CA (US); Ronald Pearl, San Clemente, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/654,273

(22) Filed: Oct. 17, 2012

(65) Prior Publication Data

US 2013/0041306 A1 Feb. 14, 2013

Related U.S. Application Data

(63) Continuation of application No. 13/101,240, filed on May 5, 2011.

(51) Int. Cl.
*A61M 19/00* (2006.01)

(52) U.S. Cl.
USPC .................................. 604/8; 604/264

(58) Field of Classification Search
USPC ............... 604/65–67, 264; 623/1.1, 1.42, 3.1; 606/153

See application file for complete search history.

(56) References Cited

U.S. PATENT DOCUMENTS

| | | | | |
|---|---|---|---|---|
| 6,315,752 | B1 * | 11/2001 | DiMatteo | 604/8 |
| 7,628,768 | B2 * | 12/2009 | Faul et al. | 604/8 |
| 7,967,769 | B2 * | 6/2011 | Faul et al. | 604/8 |
| 8,048,016 | B2 * | 11/2011 | Faul et al. | 604/8 |
| 2005/0277967 | A1 * | 12/2005 | Brenneman et al. | 606/167 |

* cited by examiner

*Primary Examiner* — Leslie Deak
(74) *Attorney, Agent, or Firm* — Adam Warwick Bell; D. Phil; James Heslin

(57) ABSTRACT

A long-term implantable arterio-venous shunt device or creation of a fistula is provided that can be used as a therapeutic method for treating chronic obstructive pulmonary disease (COPD). The shunt device is implanted between an artery and a vein, preferably between a peripheral artery and the inferior vena cava. The shunt device and method of creating a fistula increases cardiac output and decreases the systemic vascular resistance and allows a blood flow rate through the shunt device of at least 5 ml/min after the implantation. Based on the effects of the method and device to the respiratory, cardiac and circulatory system, the method and device are beneficial as a therapy to patients with problems or conditions related to these systems.

20 Claims, 13 Drawing Sheets

THERAPEUTIC METHOD FOR TREATMENT OF HYPERTENSION

This application is a continuation of, and claims priority to and the benefit of pending U.S. application Ser. No. 13/101,240 filed 5 May 2011, which is a continuation of application Ser. No. 11/789,759, filed Apr. 24, 2007, which itself is a Continuation-in-Part of U.S. patent application Ser. No. 10/961,731, filed Oct. 7, 2004, which in turn, is a Continuation-in-Part of U.S. patent application Ser. No. 10/820,169, filed Apr. 6, 2004, that claims the benefit of U.S. Provisional Patent Application Ser. No. 60/461,467, filed Apr. 8, 2003, all of which are herein incorporated by reference in their entirety.

TECHNICAL FIELD

The present invention relates to implanted medical devices. In particular, the present invention relates to an arterio-venous shunt and methods for creating a fistula between adjacent blood vessels.

BACKGROUND ART

Chronic Obstructive Pulmonary Disease (COPD) is a syndrome that may be caused by a number of different diseases, all of which damage the alveoli and bronchioles, leading to impaired lung function. These diseases include including asthmatic bronchitis, chronic bronchitis (with normal airflow), chronic obstructive bronchitis, bullous disease, and emphysema. About 11% of the population of the United States has COPD, and according to the Mayo Clinic, COPD kills about 85,000 people a year in the United States. As the alveoli and bronchial tubes are destroyed, the remaining healthy lung tissue must work harder to provide the required amount of blood oxygenation. This need for more air leads to lung over-inflation. As the lung over-expands, it gradually enlarges, completely filling the chest cavity and causing a sense of shortness of breath. The lung eventually looses its elasticity, and the combination of a larger, less elastic lung and damaged, nonfunctioning tissue leads to a slower airflow into and out of the lung, resulting in the feeling of an obstructed airway.

The present standard of care is oxygen therapy, which requires a patient to remain near a stationary oxygen source or carry a bulky portable oxygen source when away from home or a treatment facility. It is easy to appreciate that such oxygen therapy has many disadvantages.

Lung reduction surgery has recently been proposed for treating patients with chronic obstructive pulmonary disease. Such surgery, however, is not a panacea. It can be used on only a small percentage of the total patient population, requires long recovery times, and does not always provide a clear patient benefit. Even when successful, patients often continue to require supplemental oxygen therapy.

It is desirable to provide improved approaches, including both devices and methods, for treating patients suffering from chronic obstructive pulmonary disease and other related conditions.

DISCLOSURE OF INVENTION

The present invention encompasses creating a fistula between an artery and a vein, and methods of using such a fistula so created for treating chronic obstructive pulmonary disease and other conditions, for example, cardiac diseases and disorders, such as, but not limited to, congestive heart failure, heart failure, chronic hypertension, and coronary artery disease; systemic arterial hypertension, hypotension, respiratory failure, pulmonary arterial hypertension, lung fibrosis, adult respiratory distress syndrome, chronic bronchitis emphysema, emphysema, cystic fibrosis, cystic lung disease, chronic asthma, and the like. The fistula may be created between an artery and a vein, for example between the femoral artery and the saphenous vein. In a preferred embodiment the fistula is created between an artery and a vein that are "twinned" or are anatomically parallel to one another.

The present invention also encompasses implantable arterio-venous shunt devices, and methods for using such devices for treating chronic obstructive pulmonary disease and other conditions, such as congestive heart failure, systemic arterial hypertension, hypotension, respiratory failure, pulmonary arterial hypertension, lung fibrosis, adult respiratory distress syndrome, and the like. The shunt device may be implanted between an artery and a vein, for example between the aorta and the inferior vena cava.

The present invention diverts a portion of the patient's blood from the high-pressure arterial circulatory to the lower-pressure venous circulatory system. This arterio-venous shunting has several effects, including increasing the mean or average partial pressure of blood oxygen ($PaO_2$) in a patient's circulation, increasing cardiac output, decreasing systemic vascular resistance, and reducing the mean arterial pressure. In the case of patients suffering from chronic obstructive pulmonary disease, such increase in cardiac output improves the amount of oxygenated blood available to the lungs and such increase in blood oxygen relieves the shortness of breath and other symptoms suffered by the patient.

The invention further provides a therapeutic method for treating a disease or disorder in a subject, the method increasing cardiac output in the subject, the method comprising: creating a fistula between a systemic artery and systemic vein of said subject, said fistula adapted to allow blood flow rate therethrough of at least 5 ml/min, wherein said blood flow through the fistula bypasses the peripheral microcirculation, and wherein creation of said fistula results in an increase in the cardiac output in said subject. In a preferred embodiment, the disease or disorder is selected from the group consisting of chronic obstructive pulmonary disease, congestive heart failure, heart failure, chronic hypertension, and coronary artery disease; systemic arterial hypertension, hypotension, respiratory failure, pulmonary arterial hypertension, lung fibrosis, adult respiratory distress syndrome, chronic bronchitis emphysema, emphysema, cystic fibrosis, cystic lung disease, chronic asthma, and the like.

The invention also provides a therapeutic method for increasing cardiac output in a subject having disease or disorder, the method comprising: creating an arterio-venous fistula between a systemic artery and a systemic vein of said subject, wherein said fistula allows blood flow rate therethrough of at least 5 ml/min, wherein said blood flow through the fistula bypasses the peripheral microcirculation, and wherein creation of said fistula results in an increase in the cardiac output in said subject. In a preferred embodiment the disease or disorder is selected from the group consisting of chronic obstructive pulmonary disease, congestive heart failure, heart failure, chronic hypertension, and coronary artery disease; systemic arterial hypertension, hypotension, respiratory failure, pulmonary arterial hypertension, lung fibrosis, adult respiratory distress syndrome, chronic bronchitis emphysema, emphysema, cystic fibrosis, cystic lung disease, chronic asthma, and the like.

The invention still further provides an apparatus for increasing cardiac output in a subject having a disease or disorder, the apparatus comprising: an arteriovenous shunt device shaped and adapted for placement between a systemic artery and a systemic vein in said subject. In a preferred embodiment, the disease or disorder is selected from the group consisting of chronic obstructive pulmonary disease, congestive heart failure, heart failure, chronic hypertension, and coronary artery disease; systemic arterial hypertension, hypotension, respiratory failure, pulmonary arterial hypertension, lung fibrosis, adult respiratory distress syndrome, chronic bronchitis emphysema, emphysema, cystic fibrosis, cystic lung disease, chronic asthma, and the like.

BRIEF DESCRIPTION OF DRAWINGS

FIG. 10A illustrates the effect of an aorto-caval shunt upon aortic blood flow in rats having undergone several different treatments. FIG. 10B illustrates the resulting partial pressure of oxygen in arterial blood.

MODES FOR CARRYING OUT THE INVENTION

Figure 1:
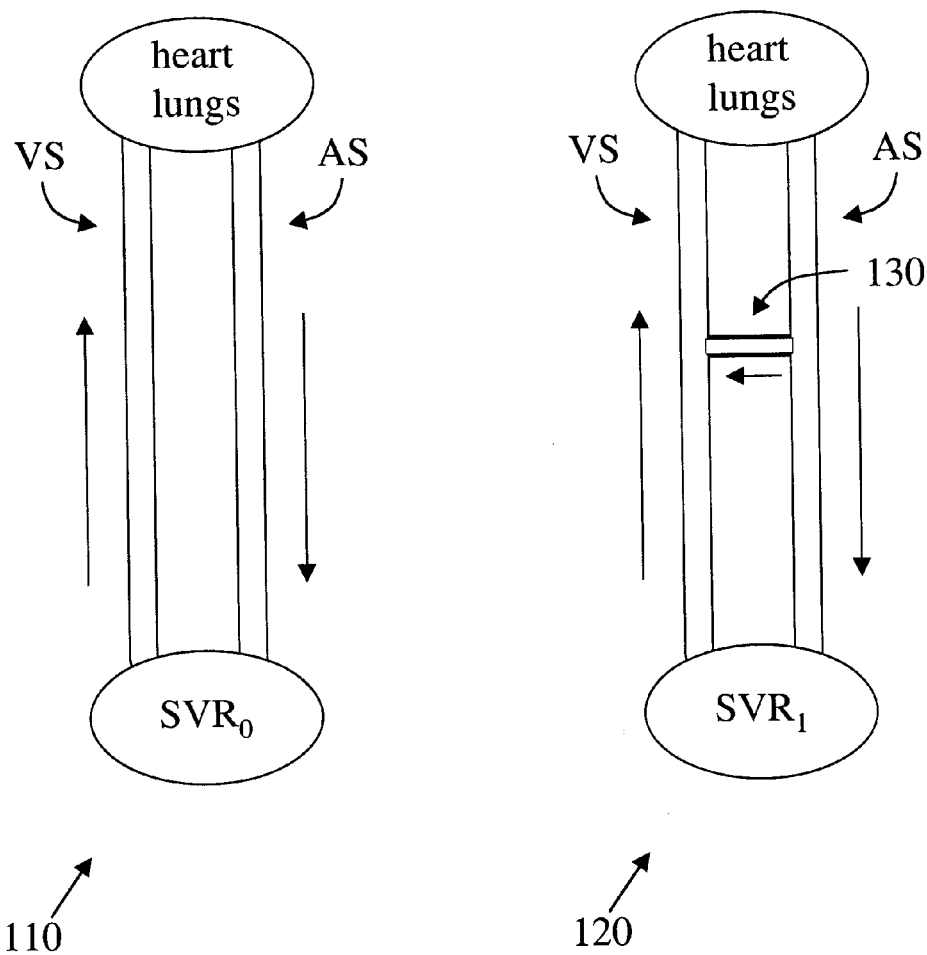
FIG. 1 is a schematic diagram showing a simplistic circulatory system with and without the shunt in place.

The invention provides implantable arterio-venous shunt devices and methods for using such devices. The shunts of the invention divert a portion of the patient's blood from the high-pressure arterial circulatory system to the lower-pressure venous circulatory system. The shunt device may be implanted between an artery and a vein, for example between the aorta and the inferior vena cava. The shunts are adapted for implantation into a human or animal subject for treating chronic obstructive pulmonary disease (COPD) and other, discussed below. The arterio-venous shunting provided by these shunts has several important physiological effects, including increasing the mean or average partial pressure of blood oxygen ($PaO_2$) in a patient's circulation, increasing cardiac output, and reducing the mean arterial pressure. In the case of patients suffering from chronic obstructive pulmonary disease, such increase in blood oxygen relieves the shortness of breath and other symptoms suffered by the patient.

The shunt device may be adapted for implantation for an extended period of at least 4 weeks, at least, or at least 3, 6, or 12 months, or even for a greater period of 3, 5, 7 or more years. Implantation may be achieved using standard open surgical procedures, or a minimally invasive surgical procedure, or an intravascular procedure.

The implantable arterio-venous shunt devices of the invention may be used to treat and alleviate the symptoms of various conditions, such as chronic obstructive pulmonary disease (COPD), congestive heart failure, systemic arterial hypertension, hypotension, respiratory failure, pulmonary arterial hypertension, lung fibrosis, adult respiratory distress syndrome, and the like. Respiratory failure is a particular condition that may be treated using the shunt of the invention. Respiratory failure is a condition characterized by a reduction in arterial oxygen concentration. The present invention treats respiratory failure by increasing the arterial oxygen content. Congestive heart failure is a condition characterized by low cardiac output. This invention treats heart failure by increasing the cardiac output. Systemic arterial hypertension is a condition characterized by a high arterial blood pressure. This invention treats systemic arterial hypertension by lowering the arterial blood pressure. Pulmonary arterial hypertension is a disease defined by an increase in pulmonary arterial pressure, which leads to reductions in cardiac output. This invention will increase venous oxygen concentration which in turn increases the oxygen content of the pulmonary arteries. The increased pulmonary arterial oxygen content, combined with the increases in cardiac output that occur after the creation of the shunt, will lower the pulmonary arterial pressure and increase the cardiac output in patients with pulmonary arterial hypertension. Pulmonary hypertension treatable by the present invention can occur (1) as a complication of a chronic hypoxia (low oxygen concentrations in arterial blood) which may be associated with chronic emphysema or chronic obstructive sleep apnea syndrome, (2) as a complication of left heart failure due to a variety of causes including mitral valve disease, (3) as a result of congenital heart disease, and (4) as a complication of abnormal increases in peripheral vascular resistance that are associated with familial pulmonary hypertension, liver cirrhosis, HIV infection, systemic sclerosis, connective tissue diseases, and prior use of diet pills.

The present invention will simultaneously cause several distinct improvements and effects on physiology: (1) an increased cardiac output (a benefit to patients with heart failure, who suffer low cardiac output), (2) a lower mean arterial blood pressure (a benefit to patients with hypertension, whose blood pressure is too high), (3) a lower diastolic blood pressure (again a benefit to patients with hypertension, whose diastolic blood pressure is too high), (4) an increased arterial oxygen concentration (a benefit to both patients with heart failure and patients with respiratory failure), and (5) a lower pulmonary arterial blood pressure (a benefit to patients with pulmonary hypertension, whose pulmonary arterial blood pressure is too high).

Methods according to the present invention for increasing the partial pressure of oxygen ($paO_2$) in circulating blood generally comprise creating a shunt to divert oxygenated arterial blood to a venous circulatory location. The amount of oxygenated arterial blood diverted may be selected based on several different criteria. In a first instance, the amount of blood diverted through the shunt may be selected to increase mean arterial $PaO_2$ by at least 5% compared to mean arterial $PaO_2$ prior to the shunt creation, preferably by at least 10%, or at least 15% or at least 20%, and often by 30% or greater. Alternatively, and often in the case of patients suffering from hypertension, the amount of blood diverted may be selected to lower mean arterial blood pressure by at least 5% compared to arterial blood pressure prior to the shunt creation, usually by at least 10%, or at least 15% or at least 20%, or at least 30% or greater. A third criteria, often useful for patients suffering from congestive heart failure, will be to create the shunt to divert oxygenated arterial blood in an amount sufficient to increase mean cardiac output by at least 5% compared to mean cardiac output prior to shunt creation, often increasing cardiac output by at least 10%, by at least 15%, or at least 20%, or at least 25%, or at least 30%, or at least 35%, or at least 45%, or at least 50%, or at least 55%, or at least 65%, or greater. Alternatively, and often in the case of patients suffering from pulmonary arterial hypertension, the amount of blood diverted may be selected to lower mean pulmonary arterial blood pressure by at least 5% compared to the pulmonary arterial blood pressure prior to the shunt creation, usually by at least 10%, or at least 20%, and often at least 30% or greater.

The shunt will typically be implanted via an open surgical procedure, via a minimally invasive surgical procedure, via an intravascular procedure, or the like. The particular procedure or method will depend on the specific arterial and venous locations that are to be connected by the shunt or shunts.

The fistula will typically be created via an open surgical procedure, via a minimally invasive surgical procedure, via an intravascular procedure, or the like. The particular procedure or method will depend on the specific arterial and venous locations that are to be connected by the fistula or fistulae.

The present invention further provides a circulatory therapy comprising creating a shunt between an arterial location and a venous location. The particular arterial and venous locations will be selected to provide the relatively high blood flow volumes which are preferred or required to achieve the therapeutic effects of the present invention. For example, the presently preferred arterial location is the aorta (either supra-renal or infra-renal) and venous location is the inferior vena cava (IVC) which can provide the desired blood flow volumes and is located close to the heart so that the diverted blood is quickly returned to the heart and lungs for further oxygenation. Other exemplary and preferred arterial and venous locations are between twinned artery and vein vessels and include: axillary artery and vein, the common iliac artery and vein, the external iliac artery and vein, the internal iliac artery and vein, the femoral artery and vein, the subclavian artery and vein, the femoral artery and saphenous vein, the brachial artery and cephalic vein, the carotid artery and the jugular vein, and other peripheral arteries and veins.

The present invention further provides a circulatory therapy comprising diverting oxygenated arterial blood to a venous location, where the amount of blood diverted is controlled in response to a measured physiological parameter. A measured physiological parameter will usually be selected to reflect the condition of the patient who is being treated. For example, a measured parameter may be blood oxygen partial pressure ($PaO_2$) in patients suffering from chronic pulmonary obstructive disease or respiratory failure due to other causes, or may be arterial blood pressure in patients suffering from systemic arterial hypertension or may be hypotension, may be cardiac output and/or heart rate in patients suffering from CHF, or may be may be pulmonary arterial pressure or pulmonary vascular resistance in patients with pulmonary arterial hypertension.

The amount of arterial blood which is diverted may be controlled by a flow control element in the shunt device implanted between the arterial blood location and the venous location. Control may be effected by particular devices including valves, pumps, controllable orifices, multiple orifices, tapering lumens, and the like. The physiologic parameters may be measured periodically or in real time. For example, the methods comprised periodically adjusting a valve or other flow component when a patient visits a patient's physician who can make the appropriate measurements. Alternatively, the measurements may be made real time by implantable sensors that control a coupled flow element.

A fistula according to the present invention is capable of carrying from about 5 ml/min or 25 ml/min or 50 ml/min to about 5000 ml/min of blood at a pressure differential of 70 mm Hg, typically from 150 ml/min to 1500 ml/min, and usually from 300 ml/min to 750 ml/min.

The present invention also provides devices. Shunts according to the present invention are preferably adapted to connect a location in a human aorta (either supra-renal or infra-renal) to a location in a human inferior vena cava to create a conduit through which blood may pass. Usually, the shunt has a lumen with a cross-sectional area in the range from 3, 5, 6, 8, or 10 $mm^2$ to 3000 $mm^2$, preferably from 20 $mm^2$ to about 1000 $mm^2$ or alternatively from 40 $mm^2$ to about 750 $mm^2$ or alternatively from 75 $mm^2$ to 500 $mm^2$, typically from 90 $mm^2$ to 300 $mm^2$, or from 100 $mm^2$ to 250 $mm^2$, or from 150 $mm^2$ to 200 $mm^2$, depending on the rate of flow desired. The lumen of the shunt device may have a length in the range from 3 mm to 20 mm, 30 mm, 50 mm, or 100 mm or more, depending on the proximity of the artery and the vein, typically from 5 mm to 10 mm.

Shunts according to the present invention are capable of carrying from about 5 ml/min or 25 ml/min or 50 ml/min to about 5000 ml/min of blood at a pressure differential of 70 mm Hg, typically from 150 ml/min to 1500 ml/min, and usually from 300 ml/min to 750 ml/min. Such shunts typically comprise a body having a lumen and in some embodiments a flow control element in the lumen. The flow control element may be a one-way control valve, typically where the valve opens at a differential pressure in the range from 50 mm Hg to 130 mm Hg, for example at a pressure of about 50 mm Hg, about 75 mm Hg, about 100 mm Hg, or about 130 mm Hg. Alternatively, the flow control element may be a flow control valve which may be connected to a pressure-responsive or other controller. Further alternatively, the flow control element may be a pump.

The inner wall of the shunt lumen will generally be smooth to prevent turbulence, and in certain embodiments may be coated with various substances such as Teflon to produce an even surface not liable to encourage clot formation, deposition of proteins and other substances and to prevent biofouling of the lumen.

In some embodiments it may be desirable to control the blood flow rate through the shunt. For this purpose a control means may be provided. The control means may be a simple on/off mechanism such as a valve or switch, or it could comprise a more sophisticated system including either an open loop control or a closed loop control with feedback provided by physiological parameters such as blood pressure and flow rate. For each level of sophistication, the control means could include a controller (ranging from a switch to a decision algorithm), one or more flow control elements that control the rate of flow through the lumen, and/or one or more sensors to provide feedback to a controller. Examples of physiological parameters that could be sensed or measure are blood pressure, heart rate, cardiac output, $PaO_2$, $O_2$ saturation, $O_2$ saturation, mean systemic arterial pressure or mean systemic venous pressure.

In an alternate embodiment, the shunt device is a self-adjustable shunt device that automatically and inherently self-adjusts its cross sectional area or its length, or both, as a function of the pressure difference across the shunt device. The self-adjustable shunt could then automatically control the blood flow rate through the shunt at a predetermined blood flow rate level or range.

The reduction of systemic vascular resistance and (controlled) blood flow through the shunt device from the arterial system to the venous system has physiological consequences on respiratory, cardiac and circulatory systems. In certain embodiments, the invention includes a respiratory or cardiorespiratory therapy producing an increase of the partial pressure of $O_2$ dissolved in the arterial blood plasma, an increase of the hemoglobin $O_2$ saturation in arterial or venous blood, or an increase of the $O_2$ concentration in arterial or venous blood. In another embodiment may include a therapy to encourage increased cardiac output. In yet another example, the method could be a circulatory therapy to decrease the pulmonary arterial blood pressure, a decrease of the systemic arterial blood pressure, a decrease of the systemic systolic pressure or a decrease of the systemic diastolic pressure. Patients with circulatory problems could benefit from such a circulatory therapy.

In use, the shunt creates allows blood flow from the arterial system to the venous system while bypassing peripheral microcirculation. Blood flow through a lumen of the device typically results on a pressure gradient between the blood in the arterial system to the blood in the venous system, indicated by the large P and small p in FIG. 1. While the pressure gradient between the arterial and venous sides of the vasculature will generally be sufficient to achieve and control the target volume of blood flow, in some instances it may be desirable to utilize a pump or other flow inducing device in order to increase or control the blood flow. Simple pumps include positive displacement pumps, such as rotary pumps, peristaltic pumps, and the like.

In general, the shunt device may be positioned between any non-cardiac artery and vein, usually an adjacent vein. In one embodiment, the device is positioned between the aorta and the inferior vena cava. In another embodiment, the device is positioned distal from the renal arteries. The device could be positioned in the pelvis to link the common iliac artery and vein, or femoral artery and vein. In another embodiment the device could be positioned in the axilla where it would link the axillary artery and vein. In yet another embodiment the device could be positioned in proximity to the clavicle and link the subclavian artery and vein.

The shunt device could be made from any biocompatible material that is strong enough or reinforced sufficiently to maintain a lumen sufficient to provide the desired blood flow volume. In one embodiment, the shunt device is made of metal, preferably titanium, surgical steel, or a nickel-titanium alloy (NiTi), while in other embodiments the device could be formed from conventional vascular graft materials. The inner surface of the lumen which conducts blood is preferably coated in whole or in part to inhibit the formation of blood clots. The surface could be coated with for instance polytetrafluoroethylene (Teflon®), or the like. The device might also be coated with antibiotic to prevent infection, and/or antiproliferative agents to prevent clot formation in the lumen.

The cross-sectional area of the lumen of the shunt device will be selected to provide a desired volumetric blood flow rate between the arterial vasculature and the venous vasculature. Typically, the lumen will have a circular cross section and a diameter in the range from 1 mm to 30 mm, typically from 2 mm to 10 mm, for example 4 mm to 6 mm. The length of the shunt device will also affect the flow resistance and thus the flow rate through the shunt. Typically, the shunt may have a length in the range from 3 mm to 60 mm, typically from 10 mm to 40 mm, for example, 20 mm to 30 mm. In some instances, of course, it may be possible to implant two or more shunt devices at different locations between the arterial and venous sides of the vasculature. In cases of such multiple shunt device implantations, the individual shunts may be implanted in close proximity to each other or may be distributed at different regions of the vasculature. The examples herein generally focus on the case where only a single shunt device has been implanted to provide the entire volume of arterial blood into the venous side of the vasculature.

The cross-sectional area of the shunt device lumen will be selected to provide a volumetric blood flow which in turn may be selected so that the heart beats at a reasonable and sustainable rate. As a person of average skill in the art would recognize, a diameter of the lumen that results in a heart rate of, for instance, 170 beats per minute would not be sustainable and should be avoided by selecting a smaller diameter. Usually, the target heart rate will be in the range from 80 to 140 beats per minute, more usually from 90 to 110 beats per minute.

FIG. 1 is a schematic diagram of the general circulation without (110) and with (120) the device in place. Blood is pumped from the heart via the arterial system (AS) to the vasculature of the tissues from which it returns to the heart via the venous system (VS) as shown by system. Blood returning to the right side of the heart is pumped to the lungs where it becomes oxygenated before returning to the left side of the heart to be pumped to the body's tissues via the arterial system. Blood flow experiences a resistance from all of the systemic vasculature, which is referred to as the systemic vascular resistance (SVR). The SVR excludes the pulmonary vasculature. The SVR plus the pulmonary vasculature resistance (PVR) is referred as total peripheral resistance (TPR). Normal SVR is 800-1300 $(dyne \times sec)/cm^5$.

The present invention decreases the SVR by having an arterio-venous shunt device 130 implanted to shunt and re-circulate blood from the arterial system to the venous system in system 120. The blood directed through the shunt 130 bypasses the peripheral circulation and therefore decreases the SVR. FIG. 1 shows a schematic diagram of a system with a shunt (120) and a system without a shunt (110) where $SVR_1$ is lower than $SVR_0$. A desirable decrease of the SVR would be at least about 5% after the implantation of shunt device 130.

In general, shunt device 110 could be implanted between a large (proximal) artery and a large (proximal) vein. The location is selected to shunt blood from the high resistance arterial system with a high oxygen concentration to the low resistance venous system with a low oxygen concentration as shown by system 120 in FIG. 2. In a preferred embodiment, implantation of shunt device 130 is between the aorta 310 and the inferior vena cava 320, either proximal of the renal arteries, or more preferably distal of the renal arteries, as shown in FIG. 3.

Figure 2:
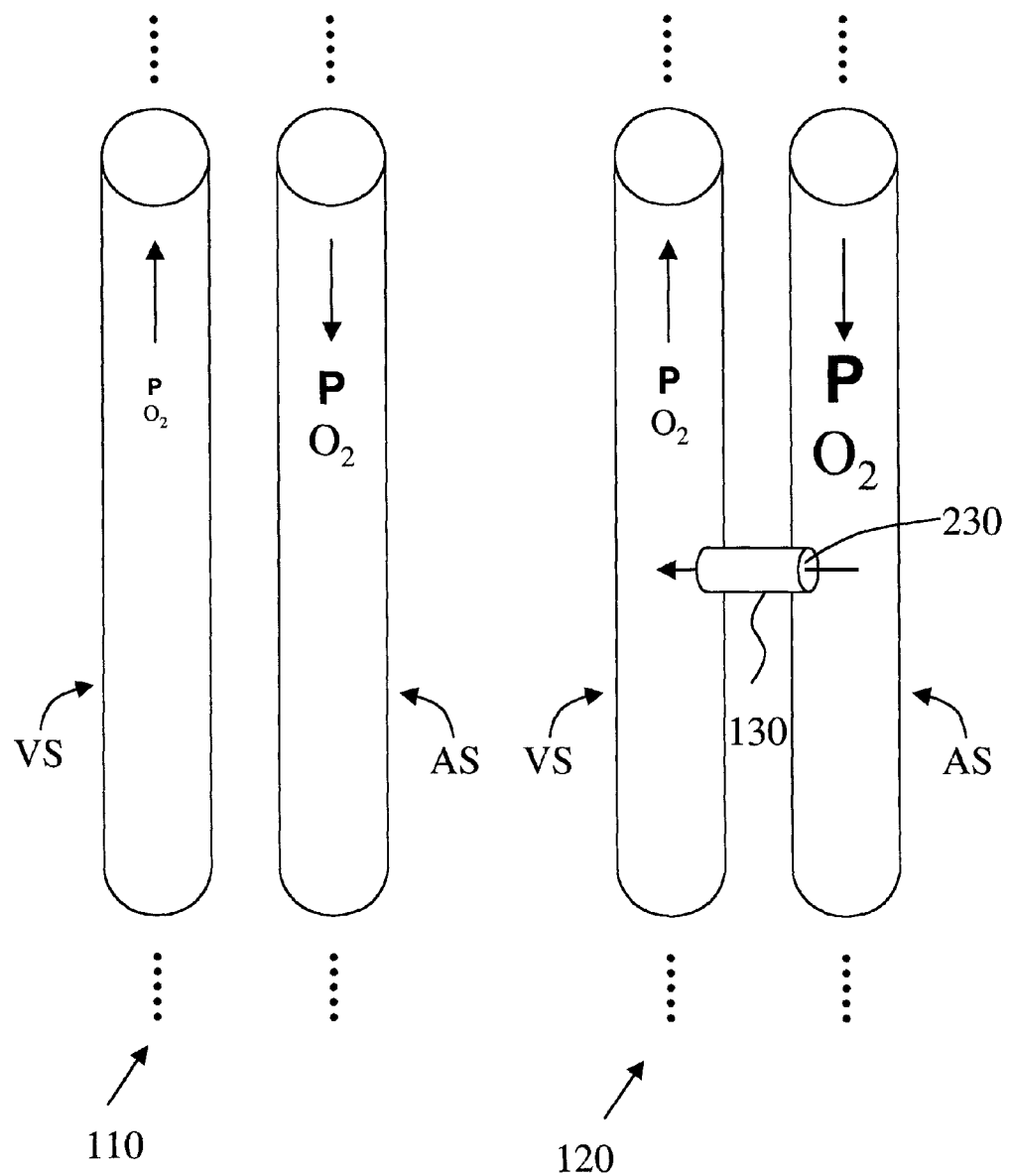
FIG. 2 is a schematic diagram showing blood flowing, with or without a shunt device of the present invention, from a high resistance arterial system with a high oxygen concentration to the low resistance venous system with a low oxygen concentration.
Figure 3:
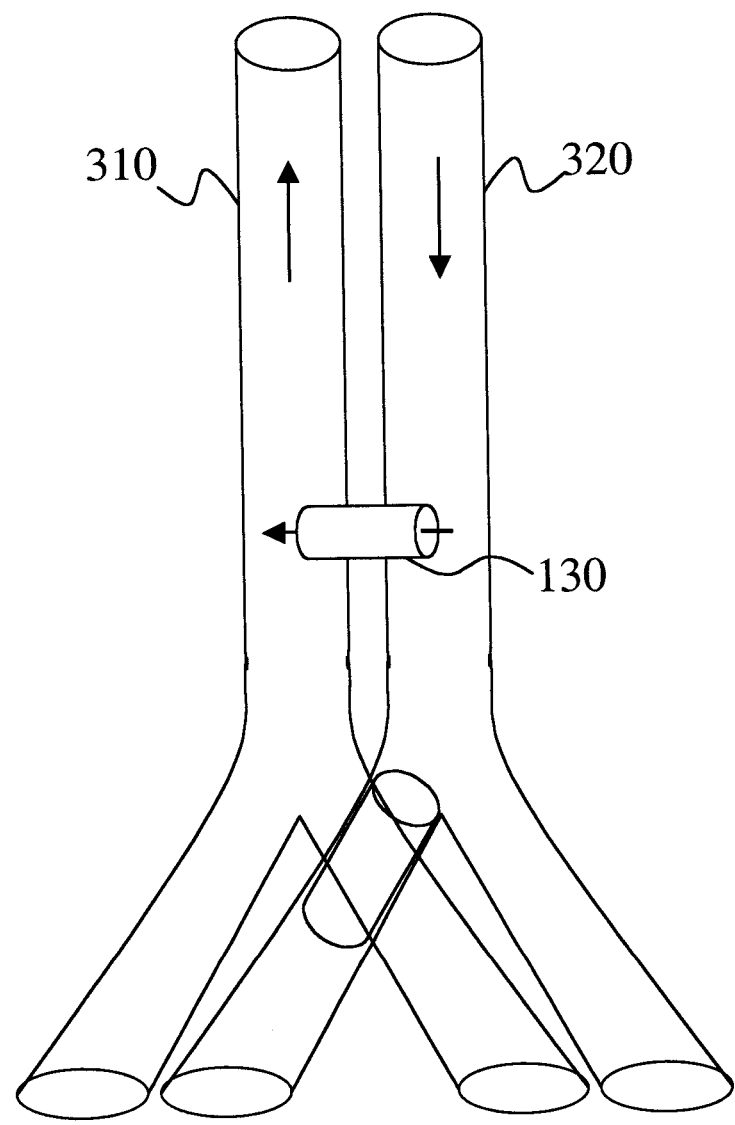
FIG. 3 is a schematic diagram showing a shunt device positioned between the aorta and inferior vena cava.

Blood flow through a lumen 230 of the shunt device 130 results from a pressure gradient between the blood in the arterial system and the blood in the venous system, indicated by the large P and small p in FIG. 2. In a preferred embodiment, the blood flow rate through shunt device is at least about 5 ml/min. While the pressure gradient between the arterial and venous sides of the vasculature will generally be sufficient to achieve and control the target volume of blood flow, the blood flow could also be regulated by a pump mechanism such as a spiral rotary pump mechanism or any other pump mechanism available in the art. In addition to the size of the lumen, the blood flow through the lumen could now also be a function on the speed of operation of the internal pump mechanism. The pump mechanism could also be electrically charged using an internal battery or by external power using a magnetic impeller, both of which are common techniques in the art.

With respect to the cardiac effects, an important consequence of decreasing the systemic vascular resistance (SVR) is that the cardiac output increases according to:

$$CO = \frac{MAP - CVP}{SVR} \times 80$$

whereby CO is cardiac output, MAP is mean arterial pressure, and CVP is central venous pressure. Since CVP is normally near 0 mm Hg, the calculation is often simplified to:

$$CO = \frac{MAP}{SVR} \times 80$$

Cardiac output is equivalent to the blood flow rate according to:

$$CO = SV * HR$$

whereby SV is stroke volume and HR is heart rate.

When SVR decreases, MAP decreases to a smaller degree. The decrease in MAP is due to a small drop in systolic pressure ($P_{systolic}$) and a larger drop in diastolic pressure ($P_{diastolic}$). $P_{diastolic}$ is dependent on the SVR whereby a drop in SVR results in a drop in $P_{diastolic}$. The pulse pressure ($P_{systolic} - P_{diastolic}$) is then increased. For instance, before implantation MAP could be 90 mm Hg and SVR could be 18 dynes, which results in a CO of 5 liters per minute. SVR of 18 dynes is determined by dividing an SVR of 1440 dynes by a conversion factor of 80. MAP of 90 mm Hg is determined by using:

$$MAP \cong P_{diastolic} + \frac{1}{3}(P_{systolic} - P_{diastolic})$$

with an exemplary PP of 30 mm Hg given a $P_{systolic}$ of 110 mm Hg and $P_{diastolic}$ of 80 mm Hg.

After implantation, SVR could for instance drop from 1440 dynes to 1000 dynes and with the conversing factor of 80 drop from 18 to 12.5. If blood pressure has a $P_{systolic}$ of 100 mm Hg over a $P_{diastolic}$ of 55 mm Hg, then MAP is 70 mm Hg; that is, in this example the $P_{systolic}$ could have dropped by 10 mm Hg, but the $P_{diastolic}$ could have dropped by 25 mm Hg. Combining these exemplary numbers would result in a cardiac output of 5.6 liters per minute; that is, 70 mm Hg divided by 12.5.

With respect to the respiratory effects, an important consequence of shunting arterial blood to the venous circulation (such as the aorta to the inferior vena cava) is that blood with high $O_2$ content circulates to the venous blood system without having the $O_2$ extracted in tissue capillaries. The $O_2$ "rich" arterial blood re-circulates to, and mixes with, the low $O_2$ concentration of the venous system. As a result, the blood flowing through shunt device 130 increases the $O_2$ concentration in the venous blood, which is illustrated by the different (font) sizes of $O_2$ in FIG. 2. The increase of $O_2$ concentration in the venous blood system leads to an increase in the $O_2$ concentration in the arterial blood in two ways, which is also illustrated by the different (font) sizes of $O_2$ in FIG. 2. First, since the blood that is shunted does not have $O_2$ extracted by tissue capillaries, the blood returning to the lungs has a higher $O_2$ concentration after the creation of the shunt than before. Second, $O_2$ is carried in the blood in two forms: (i) dissolved in arterial plasma, and (ii) bound to a protein called hemoglobin that is contained in red blood cells. Oxygen binds to hemoglobin with curvilinear kinetics, so that $O_2$ very efficiently binds to (and is carried by) hemoglobin at high $PaO_2$ (partial pressure of $O_2$ in arterial plasma), but when the $PaO_2$ is low (in particular below a $PaO_2$ of 60 mm Hg), $O_2$ is less efficiently bound to (or carried by) hemoglobin. Since the amount of $O_2$ that is bound to hemoglobin is related to the $PaO_2$, an increase in $PaO_2$ will result in greater binding of $O_2$ to hemoglobin, and increased oxygen carrying capacity.

With respect to circulatory effects, an important consequence of decreasing SVR is related to the fact that the lungs regulate their blood flow according to the $O_2$ content. A low $O_2$ content in the small pulmonary arteries impairs blood flow to the lung resulting in a high pulmonary pressure—a process called hypoxic pulmonary vasoconstriction. Therefore increasing the $O_2$ content in the pulmonary arterial blood should decrease the pulmonary arterial blood pressure. Other important circulatory consequences, as described supra with respect to cardiac consequences, are a decrease in systemic arterial blood pressure, a decrease in systemic arterial systolic pressure and/or a decrease in systemic arterial diastolic pressure.

As a person of average skill in the art would readily appreciate, the different distinct effects could be beneficial to patients with cardiac problems as a cardiac therapy, to patients with respiratory problems as a respiratory or cardio-respiratory therapy, or to patients with circulatory problems as a circulatory therapy. An illustrative list of therapies is for instance:

Cardiac Therapies.

The shunt device of the present invention could benefit patients with cardiac failure or patients who suffer from a low cardiac output (congestive heart failure) by providing an increased cardiac output.

Respiratory or Cardio-Respiratory Therapies.

The shunt device of the present invention could benefit patients with pulmonary arterial hypertension to lower pulmonary arterial blood pressure, patients with heart and/or respiratory failure by increasing arterial oxygen concentration, patients with chronic obstructive pulmonary disease by increasing of blood oxygen concentration.

Circulatory Therapies:

The shunt device of the present invention could benefit patients with hypertension to lower systemic arterial, systolic and/or diastolic blood pressure.

Other diseases or conditions that could benefit from the present invention are, for instance, hypotension (by increasing cardiac output), lung fibrosis, adult respiratory distress syndrome, and the like.

Figure 4:
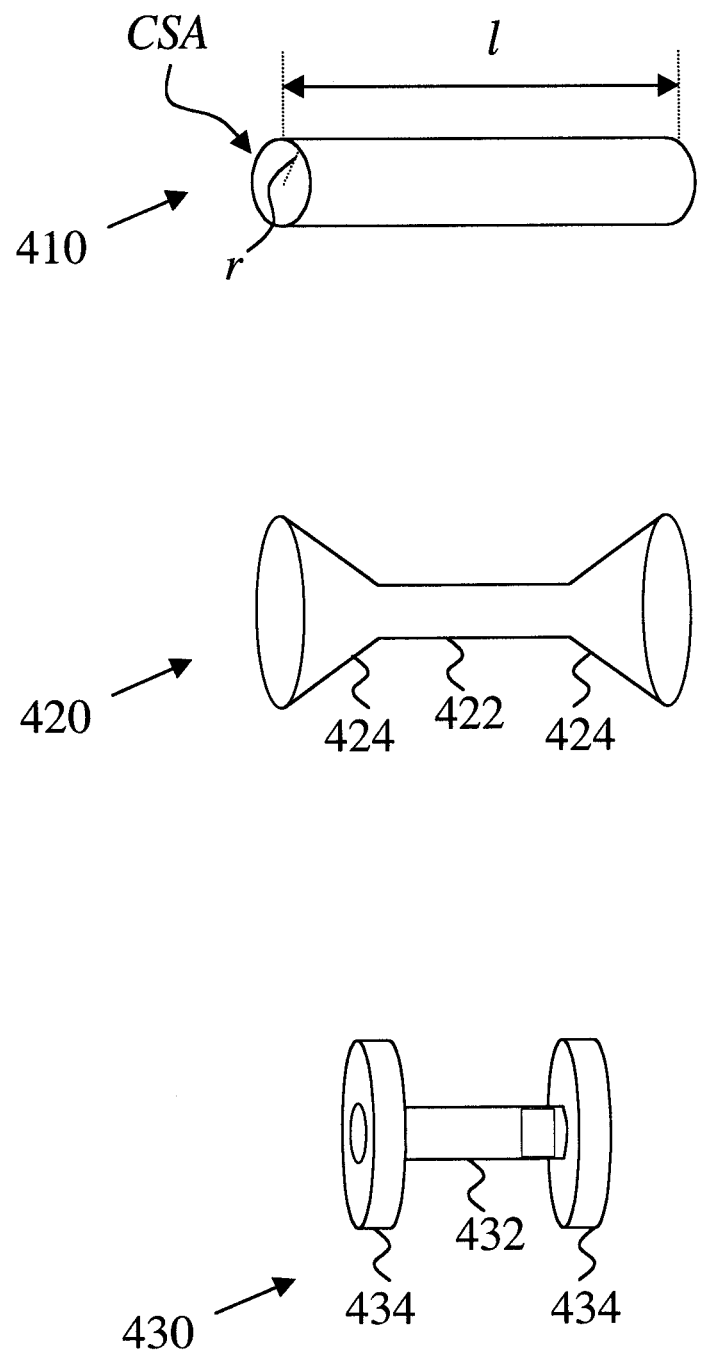
FIG. 4 is a schematic diagram showing examples of shunt devices.

The blood flow rate through the shunt device is preferably at least 5 ml/min. In case the shunt device is a cylinder then the parameters of the lumen of the shunt device that determine the blood flow rate through its lumen can be determined with the Poiseuille equation:

$$BFR = \frac{\pi \Delta P r^4}{8 \eta l}$$

whereby the volume flow rate (BFR) is a function of a blood with viscosity η, the pressure difference ΔP across the lumen of the shunt device, length l of the lumen of the shunt device and radius r of the lumen of the shunt device as shown by shunt device 410 in FIG. 4. One could also refer to the cross sectional area CSA of the lumen of shunt device 410, which is in case of a cylinder equivalent to $\pi r^2$. Generally speaking, the shape of the lumen could be a circle, an oval or any other shape as long as the requirement of blood flow is met.

In an illustrative example using the Poiseuille equation, ΔP could range from about 30 mm Hg (in someone with a MAP of 40 mm Hg and a venous pressure of 10 mm Hg) to about 150 (in someone with a MAP of 160 mm Hg and a venous pressure of 10 mm Hg). The blood viscosity could be determined in a variety of ways that could for instance be obtained from a paper by Johnston B M et al. (2004) entitled *"Non-Newtonian blood flow in human right coronary arteries: steady state simulations"* and published in *J Biomechanics* 37:709-720. With a viscosity of 0.0345P and a combination of a radius of 3 mm and a length of 3 mm of the lumen of the shunt device one would achieve a blood flow rate through the shunt of over 5 ml/min. As a person of average skill would readily appreciate, different combinations of radius and length could be determined to achieve the desired blood flow rate. In general, the length could range from about 2.5 mm to about 15 mm, and the radius could range from about 2.5 mm to about 15 mm. For the length one could determine a minimum length of for example, 2.5 mm given an exemplary wall thickness of a human adult aorta of about 1.5 mm and an exemplary wall thickness of a human adult inferior vena cava of about 1 mm. One could also express the lumen opening in terms of cross section area, which could range from about 19 $mm^2$ to about 750 $mm^2$.

The shunt device is preferably made from any biocompatible material strong enough or sufficiently reinforced to maintain a lumen that meets the desired blood flow rate. In one embodiment, the shunt device is made of metal, preferably titanium, while in other embodiments the shunt device could be formed from conventional vascular graft materials, polytetrafluoroethylene (PTFE), nickel titanium memory, elastic material, or the like. The inner surface of the shunt device is preferably coated in whole or in part to inhibit the formation of blood clots. The surface could be coated with for instance polytetrafluoroethylene (Teflon®), or similar coatings/products. The shunt device might also be coated with antibiotic to prevent atheroma, infection, and/or anti-proliferative or anti-coagulant agents to prevent clot formation in the lumen.

A secure connection between the shunt device and the artery and vein is desirable. Different techniques could be employed to provide such a secure connection. For instance, for attachment of shunt devices formed from typical fabric graft materials one could use sutures, staples, biocompatible glues, or the like. In the case of metals and other rigid materials, the shunt device could be formed with flared or flanged ends, such as the umbrella or funnel device 424 (shown in FIG. 4). Umbrella ends 424 are placed at opposite ends of a tubular element 422 that form shunt device 420. Umbrella ends 424 are positioned respectively inside the artery and inside the vein, and the tubular element connects in between the artery and the vein. In a different embodiment, umbrella ends 434 could be positioned more or less perpendicular with respect to tubular element 432 as shown in shunt device 430. The key idea is that the diameter of the securing (connection) elements is larger than the opening in the artery and vein thereby keeping the shunt device in place. The securing elements could include a mechanism that unfolds when the shunt device is in place and implanted in the artery and vein. The art teaches different techniques and securing type mechanisms that could be used in the present invention.

The shunt device(s) could be implanted in a variety of ways, including the open surgical procedures, the laparoscopic and other minimally invasive techniques, and the intravascular techniques (where all or a portion of the shunt device is introduced at least partially through the lumen of one of the blood vessels to be shunted). The shunt device could also be implanted by, for instance, a surgical procedure such as an aortic surgery. The shunt device could further be implanted through interventional procedures such as, for instance, by means of a catheter through the iliac artery and guided by fluoroscopy. The shunt device could be deployed over a guidewire (for example, the Seldinger technique) and assembled in the body through interventional radiology techniques like the opening of an umbrella. All such surgical and interventional techniques are well known in the art. It is preferred to leave the shunt device implanted in the person for a long-term period (at least 6 weeks, but most often for years).

Figure 5:
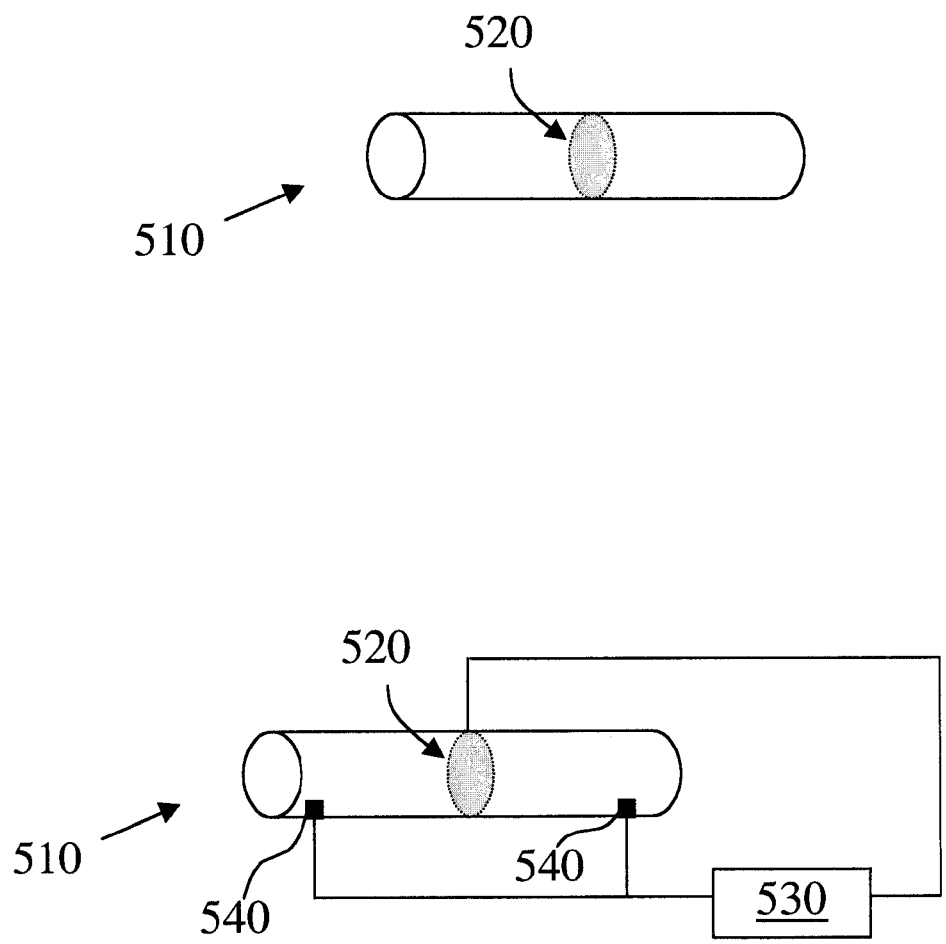
FIG. 5 is a schematic diagram showing shunt devices with a control means.

In some cases it might be desired to include a control means to control the blood flow rate with one or more flow control elements, one or more controllers and/or one or more sensors. A flow control element 520 could be placed in the shunt device 510 as shown in FIG. 5. It could be placed at either end of the shunt device or somewhere in between. In one example, the function of the flow control element could be as simple as to have an electrically, magnetically or mechanically open/close mechanism such as a switch or one-way valve. Such an open/close element could also be a hook with a lever or a gearshift. In another example, a controller 530 could be used to control the timing of opening/closing (for example, frequency and duration) or to control changes in blood flow rate. Controller 530 could control flow control element 510 such as one-way valve(s), pump(s) (positive displacement pump(s), rotary pump(s), peristaltic pump(s), and the like), controllable orifice(s) and the like. The flow control element could be electrically charged using an internal battery (for example, a lithium battery; not shown) or by external power (not shown) using a magnetic impeller, both of which are common techniques in the art.

Yet another advancement of the control means for the shunt device is to include one or more sensors 540 that provide feedback to the controller 530. The figures show two sensors, however, the present invention is not limited to two sensors and could be at least one sensor that is implanted inside the shunt device, near the shunt device, or inside or near the vasculature system. The sensor(s) could also be placed outside the body. Sensors 540 could sense (and/or measure) physiological parameter(s) in real time either periodically or continuously. The selection of one or more physiological parameters could be to reflect the condition of a person or patient who is being treated. Examples of physiological parameters that could be sensed with one or more sensors are blood pressure, heart rate, cardiac output, $PaO_2$, $O_2$ saturation, $O_2$ saturation, mean systemic arterial pressure, and/or mean systemic venous pressure. The controller could include a decision method to determine appropriate action on the flow control element. The controller could either be a stand-alone implantable controller and/or could be operated from outside the body. It might be useful to update the controller or change the current controller settings; for example, in cases when the controller controls a set-value, a particular range or critical boundaries (minima/maxima), or when the controller requires an upgrade of its code.

The controller may select different criteria that are for example, dependent on the type of disease, condition and/or desired therapy. In one example, the heart rate could be maintained at a reasonable physiological range and not exceed the person's maximum heart rate. The controller could have a target heart rate range of, for instance, 80 to 140 beats per minute, more usually from 90 to 110 beats per minute. In another example, it might be desired to increase cardiac output, partial pressure of $O_2$ dissolved in the arterial blood plasma ($PaO_2$), the hemoglobin $O_2$ saturation in arterial or venous blood, or the $O_2$ concentration in arterial or venous blood. These increases could be at least 5% compared to their value before implantation, except for $HbO_2$, which could be at least 1%. In a preferred situation these increases could be higher and on the order of 10% or 20% and up (5% and 10% for $HbO_2$). In still another example, it might be desired to decrease the pulmonary arterial blood pressure, the systemic arterial blood pressure, the systemic systolic pressure or the systemic diastolic pressure. These decreases could be at least 5% compared to their value before implantation. In a preferred situation these decreases could be higher and on the order of 10% or 20% and up. In yet another example, the blood flow rate could increase from at least 5 ml/min compared to before implantation to a situation where the shunt is capable of carrying up to 5000 ml/min of blood at for example, a pressure differential across the shunt device of 70 mm Hg.

The description supra relates to a shunt device whereby the blood flow rate could be changed and controlled. In these situations, the structural parameters of the shunt device, such as the length, cross section area and radius are fixed. However, in an alternate embodiment, described infra, the shunt device could change its cross section area, radius and/or length. This could be accomplished either in a controlled fashion, like with a controller and sensor(s) as described supra, or in a self-adjustable fashion (that is, self-organizing fashion).

Figure 6:
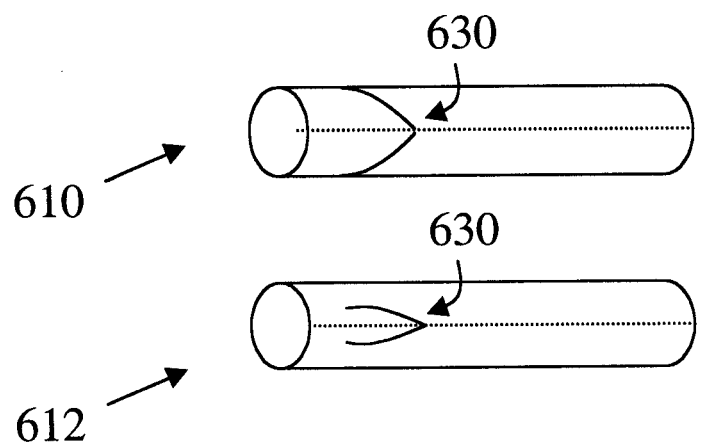
FIG. 6 is a schematic diagram showing shunt devices with a controllable or self-adjustable flow regulator.
Figure 6:
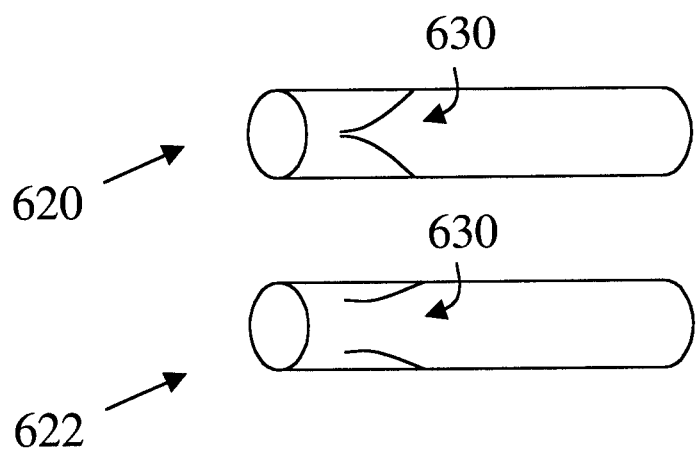
Figure 6:
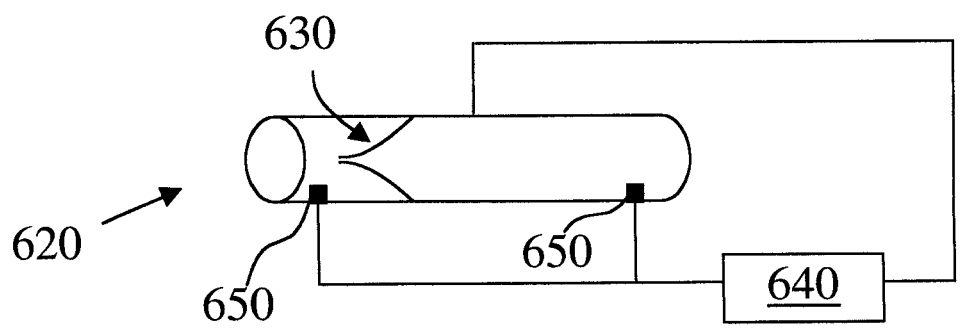

FIG. 6 shows an example of a shunt device 610, 620 with a mechanism of leaves 630 disposed in the lumen of the shunt device that could change the cross section area of the lumen. Leaves 630 could be attached to a central axis or to the inner wall of shunt device 610, 620 respectively. Two or more leaves could be used with the capability of changing their position from a closed position gradually to an open position (compare 610 and 612, and 620 and 622 respectively). The leaves in shunt devices 610, 620 could be integrated with a controller 640 and/or sensor(s) 650 in a similar fashion as described supra.

Leaves 630 could also be included as a self-adjusting mechanism for opening and closing of the shunt device. When the blood flow increases or blood pressure increases, the flexible leaves automatically open up from a more or less closed position to a more or less open position, and vice versa.

Figure 7:
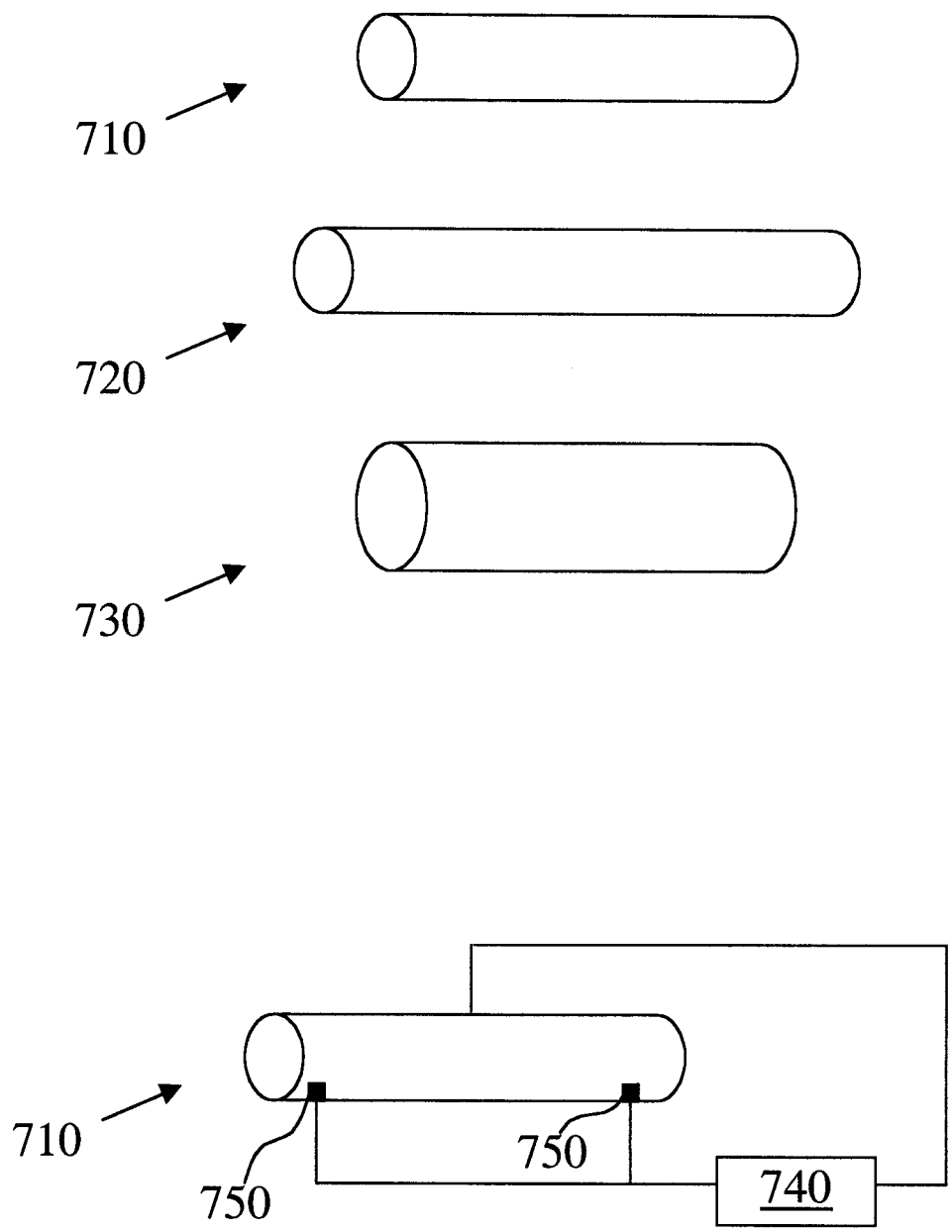
FIG. 7 is a schematic diagram showing shunt devices with a controllable flow-regulator mechanism using a smart material.

FIG. 7 shows an example of a shunt device 710 that is made of a smart material such as a memory metal/alloy that can change its length and cross sectional area (radius). For instance, shunt device 710 could be made longer as shown by 720 or wider as shown by 730 (larger cross sectional area). Shunt devices 710 could be integrated with a controller 740 and/or sensor(s) 750 in a similar fashion as described supra. Mechanisms of memory metals/alloys (including particular stent-graft materials) and their controls are known in the art.

Figure 8:
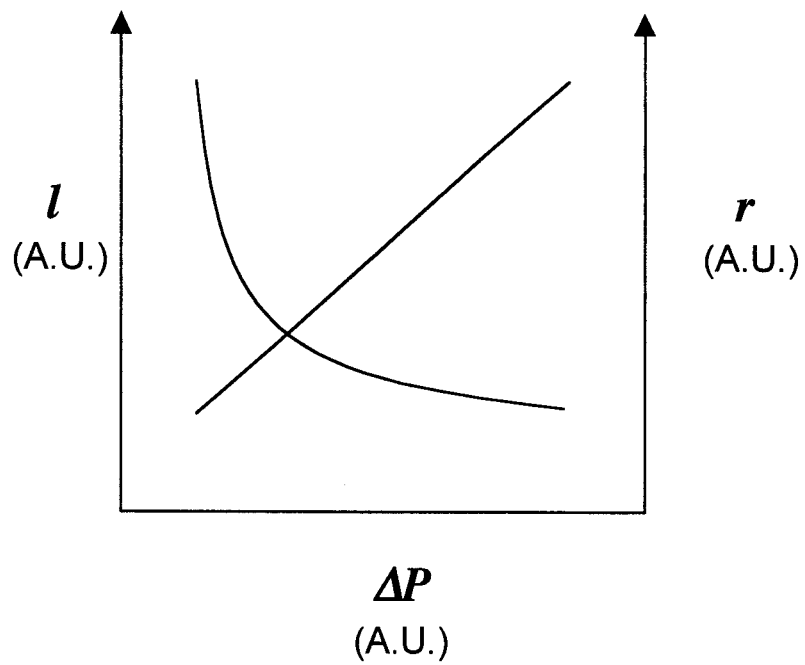
FIG. 8 is a schematic diagram showing examples of a self-adjustable shunt devices and a graph according to the Poiseuille formula used to determine change in pressure as a function of the length and radius of the shunt.
Figure 8:
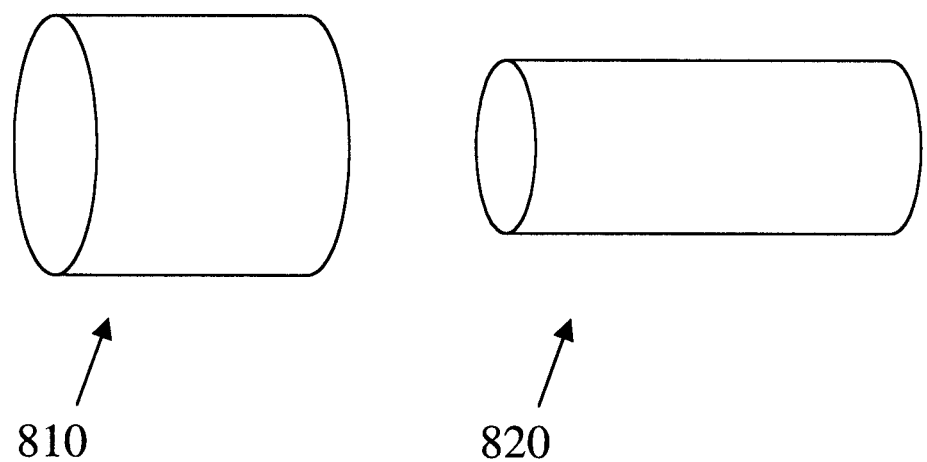

In a self-adjustable fashion it could for example, be desirable to keep the blood flow rate at a level or range across the shunt device without any controller; that is, the shunt device is self-organizing. To establish this the length and radius need to work in tandem as a function of $\Delta P$ and according to the Poiseuille equation (see supra) (see FIG. 8). For instance, length and $\Delta P$ have a linear relationship such that when $\Delta P$ increases the length increases in a linear fashion to maintain the blood flow rate at the same level, and vice versa. The radius and $\Delta P$ have an inverse non-linear relationship such that when $\Delta P$ increase the radius decreases in a non-linear fashion to maintain the blood flow rate at the same level, and vice versa. It is pointed out that the length and radius have to work in opposite and unequal value to maintain a particular blood flow rate (see supra for Poiseuille equation). Shunt device 810 should then be made of a material that is capable of increasing its length, but simultaneously decreasing its radius when $\Delta P$ increases, (indicated by changing from 810 and 820). Examples of such materials are elastic materials with reinforced filaments or fibers arranged and distributed over (or within) the shunt device (not shown in 810, 820) to ensure selected and directional changes, according to Poiseuille equation; that is, (i) an increase in cross sectional area with a decrease in length, and (ii) a decrease in cross sectional area with an increase in length.

Figure 9:
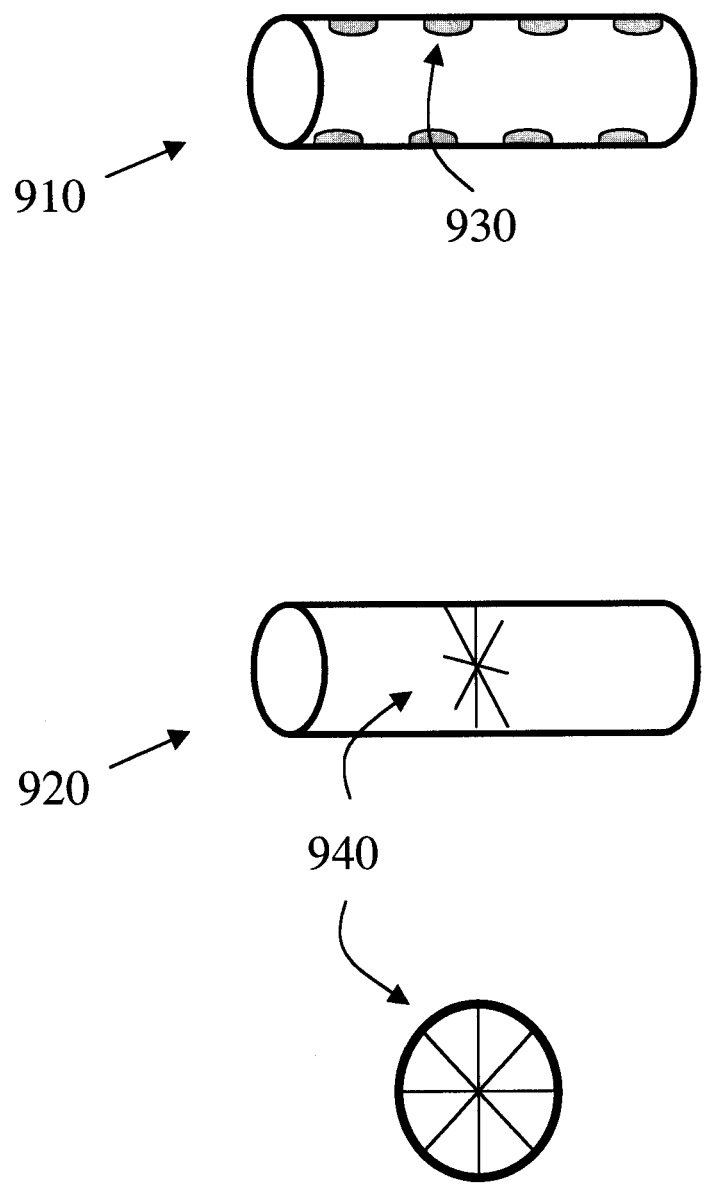
FIG. 9 is a schematic diagram showing a shunt device with a means to increase resistance to blood flow.

Other than following the Poiseuille equation one could change the blood flow rate by following Ohm's law by increasing the resistance to blood flow through the shunt device. Means to increase this resistance could for instance be accomplished by disposing roughness or obstacles such as bumps 930 or filaments/spokes 940 to the inner wall of the lumen of shunt device 910, 920 respectively as shown in FIG. 9. The blood flow could then also change from laminar flow to non-laminar flow.

Figure 13:
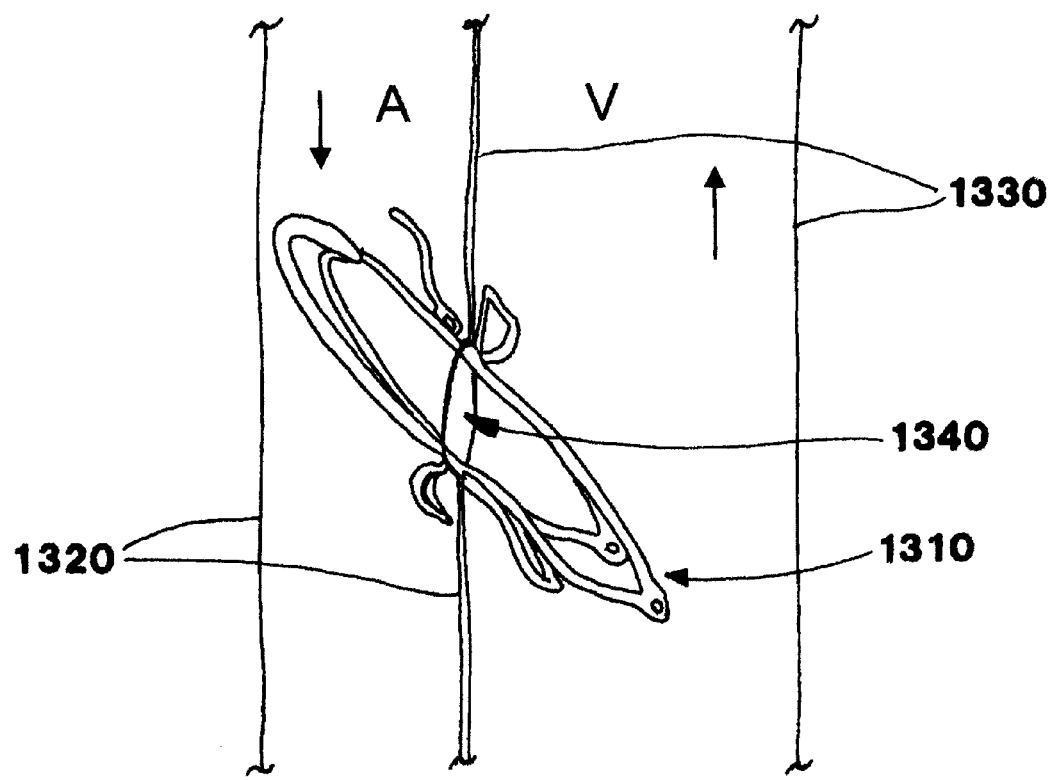
FIG. 13 illustrates an exemplary device used to create a fistula, a percutaneous anastomotic clip.

One method for creating a fistula can include use of a device having curved arms that secure the device between the artery and vein and form a predictable 5 mm diameter lumen between a vein and an artery that are twinned or anatomically adjacent to one another along a portion of their length. Such a device can be an anastomotic clip as illustrated in FIG. 13. Such a clip can comprise a memory-shape alloy such as a NiTi alloy (Nitinol®). In the alternative, the device can be manufactured using another metal alloy or a substantially pure metal, such as stainless steel, or from a composite material. Such alloys, substantially pure metals, and composite materials are well known to those of skill in the art.

Animal Studies

Figure 10:
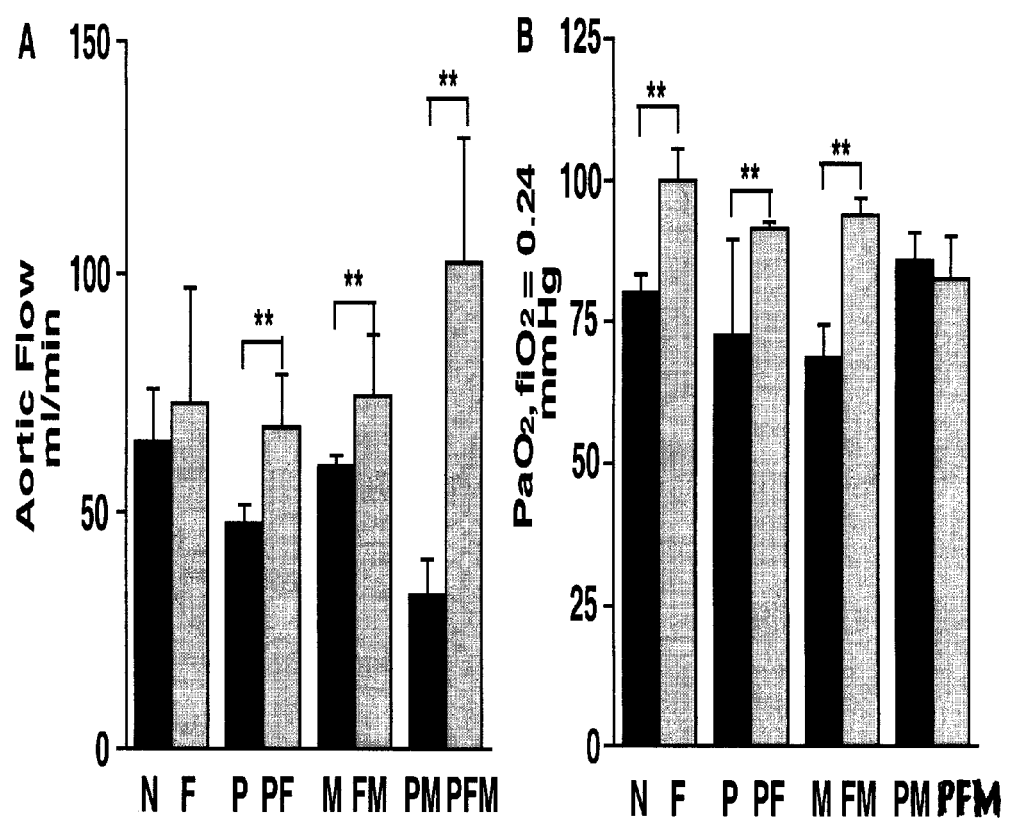
FIG. 10 shows the results from animal experiments regarding some physiological effects of an aorto-caval shunt in rats according to the present invention.
Figure 11:
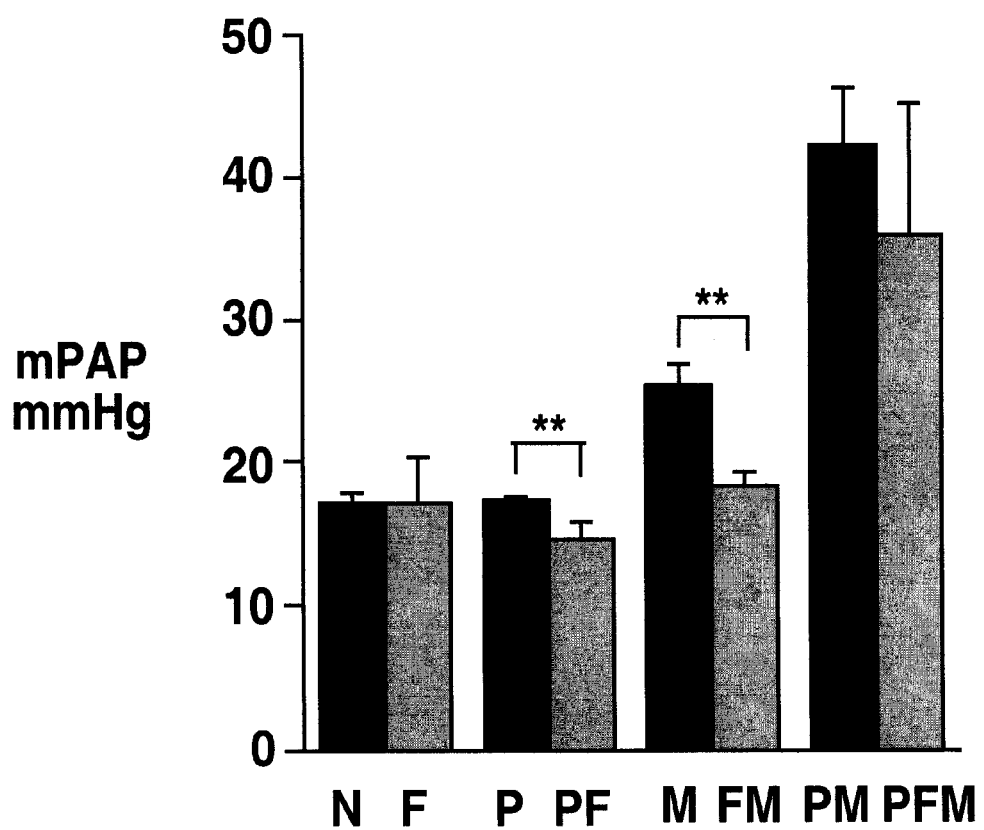
FIG. 11 shows the results from animal experiments regarding the effect of an aorto-caval shunt in rats upon mean pulmonary artery pressures according to the present invention.
Figure 12:
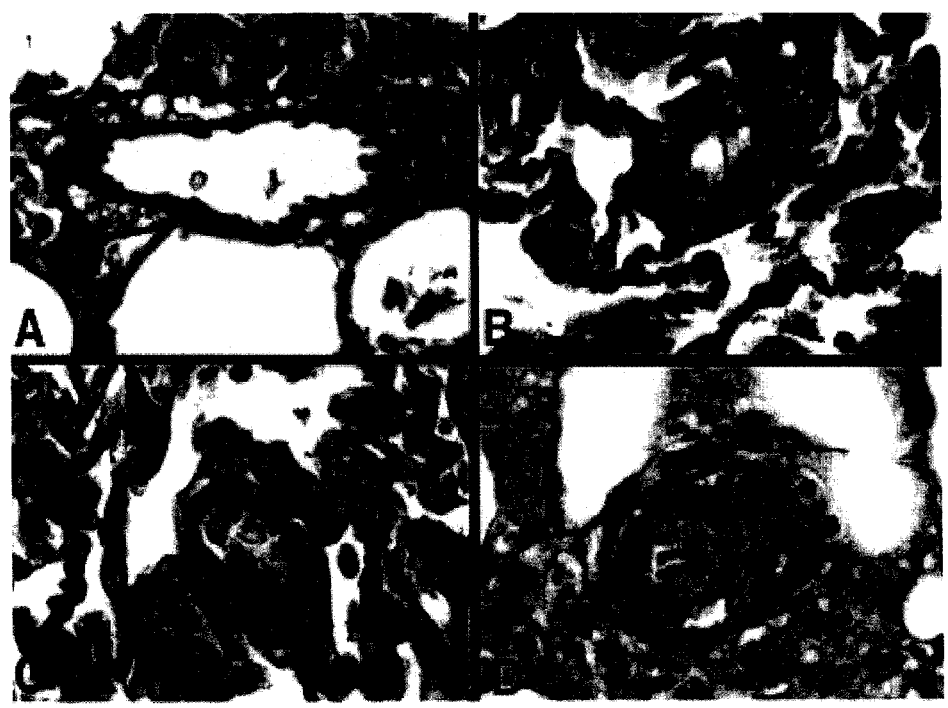
FIG. 12 illustrates four photomicrographs of small pulmonary arteries (A-D) to show the cytological effects of creating an aorto-caval shunt in rats according to the present invention.

FIGS. 10-12 show additional information regarding some physiological effects of an aorto-caval shunt in rats. These effects are the result of a study performed by the inventors of the present invention. FIG. 10 shows the effect of an aorto-caval shunt on several groups of experimental animals. In each group the presence of an aorto-caval shunt was associated with increased aortic blood flow (AF) and with increased partial pressure of oxygen in arterial blood ($PaO_2$) in rats that were receiving supplemental oxygen ($FiO_2$=0.24, or the fraction of inspired oxygen was 24%). Measurements of: (A): Aortic flow (24% $O_2$) and (B): Arterial blood oxygen tension ($FiO_2$=0.24) ($PaO_2$). Note that groups PM and PFM received $FiO_2$=0.50 during experimentation. Group N represents normal rats (n=6), Group F underwent aorto-caval shunt (n=6), Group P underwent left pneumonectomy (n=6), Group PF underwent left pneumonectomy and the creation of an aorto-caval shunt (n=6), Group M received a toxin that causes pulmonary hypertension called monocrotaline (n=6), Group FM underwent aorto-caval shunt and received monocrotaline (n=6), Group PM underwent left pneumonectomy and received monocrotaline (n=6), Group PFM underwent left pneumonectomy and the creation of an aorto-caval shunt and then received monocrotaline (n=6). (**=p<0.01).

FIG. 11 shows the effect of the presence of an aorto-caval shunt in several groups of experimental animals. Aorta-caval shunta attenuates the development of pulmonary arterial hypertension. The measurements shown in FIG. 11 are of mean pulmonary artery pressures (PAP). Group N represents normal rats (n=6), Group F underwent aorto-caval shunt (n=6), Group P underwent left pneumonectomy (n=6), Group PF underwent left pneumonectomy and the creation of an aorto-caval shunt (n=6), Group M received monocrotaline (n=6), Group FM underwent aorto-caval shunt and received monocrotaline (n=6), Group PM underwent left pneumonectomy and received monocrotaline (n=6), Group PFM underwent left pneumonectomy and the creation of an aorto-caval shunt and then received monocrotaline (n=6). (*=p<0.05, **=p<0.01).

FIG. 12 shows photomicrographs of small pulmonary arteries (A-D). (A) shows an example that normal rat (group N) arterioles do not have evidence of neointimal formation (grade 0). (B) shows an example of a grade 1 neointimal lesion (<50% occlusion) seen in rats that received monocrotaline alone (group M). (C) shows an example of grade 1 neointimal lesion (<50% occlusion) seen in rats that underwent left pneumonectomy and the creation of an aortocaval shunt (ACF) and then received monocrotaline (group PMF). (D) shows an example of a grade 2 neointimal lesion (>50% occlusion) seen in rats that underwent left pneumonectomy and received monocrotaline (group PM). All photomicrographs (×400), elastin van Gieson stain.

In additional experiments that further demonstrated the efficacy of the invention, seven pigs (approximately 60 kg each and having an average age of about 17 weeks) underwent surgery to create an arterio-venous fistula between the iliac artery and iliac vein with a fistula approximately 10 mm×3-4 mm. Animals were rested for three hours after surgery. With the animal under general anesthesia and neuromuscular paralysis, hypoventilation was induced via low tidal volume ventilation (3-4 ml·kg$^{-1}$·min$^{-1}$, 15 breaths·min$^{-1}$) on room air. Measures of arterial and venous oxygen saturations, cardiac output, heart rate, mean arterial pressure, and mean pulmonary arterial pressure were recorded after an hour of hypoventilation and again after a further twenty minutes of hypoventilation during which the arterio-venous fistula was occluded by inflating an intra-lumenal balloon catheter. Results are shown in Table 1.

TABLE 1

| | Patent AV fistula | Closed AV fistula | p value |
|---|---|---|---|
| Cardiac output (liters · min.$^{-1}$) | 9.3 (2.8) | 7.7 (2.4) | p < 0.001 |
| Heart rate (beats · min.$^{-1}$) | 97 (18) | 95 (20) | NS |
| Systolic pressure (mmHg) | 92 (11) | 95 (5) | NS |
| Diastolic pressure (mmHg) | 49 (8) | 59 (11) | P < 0.05 |
| Mean arterial pressure (mmHg) | 64 (6) | 74 (10) | p < 0.05 |
| Mean PAP (mmHg) | 29 (5) | 32 (8) | NS |
| SvO2% | 63 (7) | 48 (12) | p < 0.01 |
| SpO2% | 89 (8) | 79 (11) | p < 0.05 |
| paO2 (mmHg) | 67 (12) | 51 (11) | p < 0.01 |
| DO2 (ml · min.$^{-1}$) | 2.6 (0.8) | 2.0 (0.7) | P < 0.001 |

Data are shown as mean (S.E.M.); n = 7

Acute closure of the fistula led to a reduction in cardiac output (mean of 17%: range 7% to 27%). The diastolic arterial pressure increased from a mean of 50 mmHg to 60 mmHg. Acute closure of the fistula was associated with reductions in both mixed venous and arterial oxygen saturations. There was no significant change in either pulmonary artery pressure or heart rate. It was concluded that during hypoventilation a patent arterio-venous fistula increases cardiac output and oxygen delivery and therefore that an arterio-venous fistula can improve oxygen delivery in patients with chronic lung disease who suffer hypoventilation.

Clinical Studies

Clinical studies also demonstrated the efficacy of the invention. We studied the effect of a femoral arteriovenous fistula on exercise tolerance and quality of life in patients with severe oxygen dependent COPD. We created arteriovenous fistulas (ranging from 2 mm to 6 mm diameter) by anastomosing the right saphenous vein (in an end-to-side anastomosis) to the right femoral artery. Some patents received a fistula between the brachial artery to the cephalic vein. Patients were evaluated at six and at twelve weeks following creation of the fistula. The primary outcomes were changes in six minute walk distance, oxygen delivery using cycle ergometry, and quality of life (QOL) measure using the St. George's Respiratory Questionnaire (SGRQ). The secondary outcome was change in cardiac output.

See FIG. 13 for an example of how a fistula was created between adjacent artery and vein using an anastomotic clip. As shown in FIG. 13, the clip 1310 is viewed from the side penetrating the adjacent arterial (A) wall 1320 and venous (V) wall 1330 to create a fistula 1340. Vertical arrows indicate direction of fluid flow in the blood vessel.

In the initial studies, seven patients with severe COPD (mean FEV$_1$=22%; DLCO=40%, room air paO$^{2=56}$ mmHg) underwent surgery to create a femoral arteriovenous fistula. Patientw were typically discharged within two days post-surgery (post-OP). One patient was withdrawn due to a new diagnosis of lung cancer. Four patients developed blood flow through the fistula of greater than 600 ml·min$^{-1}$ (increasing cardiac output by between 15% and 65%) and all demonstrated clinically significant improvements in both quality of life (median reduction in SGRQ=12 points; spread 0-30) and six minute walk (6MWT) distance (median increase in 6MWT distance=73 m). Two patients who underwent surgery, but in whom the fistula was very small or had closed, did not improve (mean reduction in SGRQ=3; mean increase in 6MWT=0 m). A clinically significant reduction in SGRQ is 3.

Further studies included an additional five COPD cases with the above seven patients. The results of the 6MWT and QOL are shown in Table 2.

TABLE 2

| Patient No. | Fistula Size | Months Post-OP | 6MWT/m | QOL/SGRQ |
|---|---|---|---|---|
| 1 | 5 mm | 13 | 215 | −30 |
| 12 | 5 mm | 3 | 120** | N/A |
| 6 | 4 mm | 9 | 86 | −7 |
| 9 | 4 mm | 4 | 64 | −14 |
| 2 | 4 mm* | 13 | 59 | −4 |
| 8 | 4 mm | 4 | 50 | N/A |
| 4 | 5 mm | 12 | 48 | −17 |
| 13 | 4 mm | 3 | 36** | N/A |
| 5 | 3 mm | 11 | 5 | −3 |
| 3 | 0 mm* | 12 | −6 | −3 |
| 7 | 5 mm | 5 | Retest*** | −15 |
| 10 | 4 mm | 4 | Exac Retest | −19 |

Notes:
*= fistula closed;
**= results at six weeks;
***= arythmia, a clinically significant reduction in SGRQ is 3.

Significantly, of those patients still having a patent fistula, a majority showed improved 6MWT (5/10: distance>54 m;

range 59 m to 215 m; mean 109 m (±63)) and QOL (7/9: SGQR>-4; range -4 to -30; mean -15 (±9)). The biological mechanism of increasing cardiac output and decreasing systemic blood pressure resulting from creation of a fistula is probably due to physiological interactions between a number of different responses, including decreased pressure resistance from the capillaries and microcapillaries, decreasing systemic blood pressure, and reduced thickness of the myocardium.

We concluded that a femoral arteriovenous fistula can improve patients with end-stage COPD.

The present invention has now been described in accordance with several exemplary embodiments, which are intended to be illustrative in all aspects, rather than restrictive. Thus, the present invention is capable of many variations in detailed implementation, which may be derived from the description contained herein by a person of ordinary skill in the art. For example, in some instances, it may be possible and desirable to implant two or more shunt devices at different locations between the arterial and venous sides of the vasculature. In cases of such multiple shunt device implantations, the individual shunts may be implanted in close proximity to each other or may be distributed at different regions of the vasculature.

In another aspect, it should be pointed out that the present invention could be used as preventative care or as a therapy for a condition or disease. Furthermore, as a person of average skill would readily appreciate, the long-term implantable shunt device could be beneficial to improve the performance in athletes, military service personnel, performance animals (for example, dogs and horses).

The preferred location of the shunt device is between the aorta and inferior vena cava as described supra. However, it would be feasible to implant one or more shunt devices for a long-term period in the pelvis area to link the common iliac artery and vein or femoral artery and vein. In another embodiment the shunt device could be positioned in the axilla and it would link the axillary artery and vein. In yet another embodiment the device could be positioned close to the clavicle and link the subclavian artery and vein.

While the above is a complete description of the preferred embodiments of the invention, various alternatives, modifications, and equivalents may be used. Therefore, the above description should not be taken as limiting the scope of the invention which is defined only by the claims and any amendments thereto.

The invention claimed is:

1. A therapeutic method comprising:
   selecting a human subject suffering from systemic arterial hypertension; and
   diverting a portion of an oxygenated blood flow from an arterial location to a venous location in the patient by way of a flow pathway between a peripheral vein and a peripheral artery, distal from the renal arteries, wherein said diversion results in lowering systemic arterial, systolic and/or diastolic blood pressure.

2. The method of claim 1 wherein the flow pathway is between a peripheral vein and a peripheral artery, distal from the renal arteries.

3. The method of claim 1 wherein the flow pathway has a length defined by the combined wall thickness of a human artery and a human vein.

4. The method of claim 1 wherein the flow pathway is created between the common iliac artery and vein.

5. The method of claim 1 wherein the flow pathway is created between the external iliac artery and vein.

6. The method of claim 1 wherein the flow pathway is created between the internal iliac artery and vein.

7. The method of claim 1 wherein the flow pathway is created between the femoral artery and vein.

8. The method of claim 1 wherein the flow pathway provides a blood flow rate in the range from 150 ml/min to 1500 ml/min.

9. The method of claim 1 wherein said method provides a lower mean arterial blood pressure by at least 5% compared to mean arterial blood pressure prior to the flow pathway creation.

10. The method of claim 1 wherein said method provides a decrease in the systemic vascular resistance by at least 5% compared to vascular resistance prior to the flow pathway creation.

11. The method of claim 1 wherein the peripheral artery is selected from the group consisting of the common iliac artery, the external iliac artery, and the femoral artery.

12. The method of claim 1 wherein mean cardiac output is increased by at least 5% compared to mean cardiac output prior to the creation of the flow pathway.

13. The method of claim 1 wherein the flow pathway so created has a length in the range of about 2.5 mm to about 15 mm.

14. A therapeutic method for lowering systemic arterial, systolic and/or diastolic blood pressure in a human subject, the method comprising:
    selecting a subject suffering from systemic arterial hypertension, and
    creating a fistula between a peripheral artery and a peripheral vein of said subject, said fistula adapted to allow a blood flow rate therethrough of at least 5 ml/min, wherein said blood flow through the fistula bypasses the peripheral microcirculation, and wherein creation of said fistula results in lowering systemic arterial, systolic and/or diastolic blood pressure of the subject.

15. The method as set forth in claim 14, wherein the fistula forms a lumen between the artery and the vein, the lumen having a length of between 2.5 mm and 15 mm.

16. The method of claim 15 wherein the artery and the vein are both of the same type and are selected from the group consisting of: an iliac artery and an iliac vein, and a femoral artery and a femoral vein.

17. The method of claim 15 wherein the artery is either the iliac artery or the femoral artery, and the vein is either the iliac vein or the femoral vein.

18. The method of claim 15 wherein the artery and the vein are both of the same type and are selected from the group consisting of: an axiliary artery and an axiliary vein, and a subclavian artery and a subclavian vein.

19. The method as set forth in claim 15, wherein the method lowers mean arterial blood pressure of the subject by at least 5%.

20. The method as set forth in claim 15, wherein the fistula is created via an open surgical procedure, a minimally invasive surgical procedure, or an intravascular procedure.

* * * * *